United States Patent
Heo et al.

(10) Patent No.: US 11,261,417 B2
(45) Date of Patent: Mar. 1, 2022

(54) BIOREACTION CONTAINER

(71) Applicants: SPL CO., LTD., Gyeonggi-do (KR); E-CELL CD., LTD., Gyeonggi-do (KR); INDUSTRY ACADEMY COOPERATION FOUNDATION OF SEJONG UNIVERSITY, Seoul (KR)

(72) Inventors: Sang Oh Heo, Gyeonggi-do (KR); Dong Hoon Kim, Gyeonggi-do (KR); Doo Hyun Kim, Seoul (KR); Duk Jae Oh, Seoul (KR)

(73) Assignees: SPL Co., Ltd., Gyeonggi-do (KR); E-Cell CD., Ltd., Gyeonggi-do (KR); Industry Academy Cooperation Foundation of Sejona University, Seoul (KR)

( * ) Notice: Subject to any disclaimer, the term of this patent is extended or adjusted under 35 U.S.C. 154(b) by 227 days.

(21) Appl. No.: 16/462,637

(22) PCT Filed: Nov. 7, 2017

(86) PCT No.: PCT/KR2017/012549
§ 371 (c)(1),
(2) Date: May 21, 2019

(87) PCT Pub. No.: WO2018/097510
PCT Pub. Date: May 31, 2018

(65) Prior Publication Data
US 2020/0071654 A1    Mar. 5, 2020

(30) Foreign Application Priority Data

Nov. 23, 2016    (KR) .......................... 10-2016-0156724

(51) Int. Cl.
*C12M 1/34*    (2006.01)
*B01D 46/10*    (2006.01)
(Continued)

(52) U.S. Cl.
CPC ............. *C12M 41/26* (2013.01); *B01D 46/10* (2013.01); *B01F 5/0606* (2013.01); *C12M 23/38* (2013.01);
(Continued)

(58) Field of Classification Search
CPC .... B01D 46/10; B01F 5/0606; B01F 11/0014; B01F 2215/0036; C12M 23/08;
(Continued)

(56) References Cited

U.S. PATENT DOCUMENTS 5,846,817 A * 12/1998 Mausli .................. C12M 41/40
435/293.1
2016/0152936 A1 * 6/2016 Bargh .................... C12M 29/00
435/289.1

FOREIGN PATENT DOCUMENTS

GB    2495934 A  *  5/2013  ............ C12M 23/38
JP    2006094758 A    4/2006
(Continued)

OTHER PUBLICATIONS

International Search Report issued in PCT/KR2017/012549 dated Feb. 9, 2018, 5 pages.
(Continued)

*Primary Examiner* — Michael L Hobbs
(74) *Attorney, Agent, or Firm* — RatnerPrestia

(57) ABSTRACT

A bioreaction container including a culture chamber configured to contain a culture solution and a life form in an inner space, the culture chamber having an open upper end; a chamber cover portion coupled to the upper end of the culture chamber, the chamber cover portion having a protruding tube provided on one side thereof so as to communicate with the inner space; a filter cap coupled to the protruding tube in an attachable/detachable manner so as to open/close the protruding tube; a gas introduction portion
(Continued)

configured to penetrate the chamber cover portion and to communicate with the inner space so as to supply a predetermined gas into the inner space; and an acidity/basicity adjustment portion installed on the chamber cover portion while containing an adjustment solution that adjusts pH of the culture solution such that the adjustment solution is discharged into the inner space by pneumatic pressure.

12 Claims, 8 Drawing Sheets

(51) Int. Cl.
*B01F 5/06* (2006.01)
*C12M 1/00* (2006.01)
*C12M 1/12* (2006.01)

(52) U.S. Cl.
CPC ............ *C12M 37/02* (2013.01); *C12M 41/34* (2013.01); *C12M 41/40* (2013.01); *B01F 2215/0036* (2013.01)

(58) Field of Classification Search
CPC ...... C12M 23/38; C12M 27/22; C12M 29/14; C12M 37/02; C12M 41/12; C12M 41/26; C12M 41/34; C12M 41/40
See application file for complete search history.

(56) References Cited

FOREIGN PATENT DOCUMENTS

| KR | 20020083558 A | 11/2002 | |
|---|---|---|---|
| KR | 20100088297 A | 8/2010 | |
| KR | 20110098622 A | 9/2011 | |
| KR | 20160080543 A | 7/2016 | |
| WO | 2012134778 A1 | 10/2012 | |
| WO | WO-2012134778 A1 * | 10/2012 | ............ C12M 27/12 |

OTHER PUBLICATIONS

International Written Opinion issued in PCT/KR2017/012549 dated Feb. 9, 2018, 16 pages.
Notification of Reasons for Refusal issued in Korean Patent Application No. 10-2016-0156724 dated May 9, 2017, 4 pages.
Grant of Patent issued in Korean Patent Application No. 10-2016-0156724 dated Jul. 30, 2017, 1 page.

* cited by examiner

BIOREACTION CONTAINER

STATEMENT REGARDING GOVERNMENT SPONSORED RESEARCH

This invention was made with the support of the Ministry of Trade, Industry and Energy of the Republic of Korea, Grant Number 10067242. The Government has certain rights in this invention.

CROSS REFERENCE TO RELATED APPLICATIONS

This application is the U.S. National Phase Application of PCT/KR2017/012549, filed Nov. 7, 2017, which claims priority to Korean Patent Application No. 10-2016-0156724, filed Nov. 23, 2016, the contents of such applications being incorporated by reference herein.

BACKGROUND OF THE INVENTION

1. Field of the Invention

The present disclosure relates to a reaction container, a plurality of which is mounted and used on a bioculture device having a shaking function, a temperature-maintaining function, or the like in order to culture microorganisms, such as animal cells, bacteria, and viruses. More particularly, the present disclosure relates to a bioreaction container configured in such a structure that real-time monitoring of the culture environment, such as the temperature of the culture medium inside the container, the amount of dissolved oxygen, pH level, maintaining an appropriate culture temperature, supplying necessary gases, and real-time pH control can be conducted simultaneously while a culture solution and a life form are contained therein, and sampling can also be conducted easily.

2. Description of the Prior Art

The bioindustry is an industry that aims to improve life forms per se or functions unique thereto so as to produce large amounts of materials that exist in very small quantities in natural environments or to manufacture useful life forms. There has recently been extensive research in this field in connection with pharmaceuticals, chemicals, foods, and fibers.

Particularly, in the pharmaceutical product manufacturing field, genetic recombination technology has enabled mass production of insulin, which is indispensable in the treatment of diabetes, and interferons, which can be used to treat cancer, on commercial scales. In addition, ongoing basic research on biotechnology in the fields of agricultural or chemical engineering makes it possible to expect increased food production or reduced energy consumption in chemical synthesis processes in the near future.

Technologies constituting the backbone of bioindustry include gene recombination technology, which extracts only specific genetic information from a life form and inserts the same into genes of microorganisms (for example, *E. coli*) that proliferates rapidly, cell fusion technology, technology for culturing a large amount of useful life forms, and a technology related to bioreactor devices.

In the bioreactor device field, research and development regarding technology for enabling laboratory-based culture of life forms while monitoring the same in real time under optimal conditions has been ongoing, and various kinds of bioculture devices have been commercialized and used.

Prior art documents related to such bioreactor devices include Korean Patent Publication No. 10-2016-0080543 (Publication Date: Jul. 8, 2016), which is incorporated by reference, which discloses a cell culture device including: a reaction tank having a rotating shaft formed thereon and connected to a motor formed on the upper portion thereof so as to rotate, and having an agitator formed on one side of the rotating shaft and rotated such that microorganisms can undergo metabolism in a complete medium; a sparger tube provided inside the reaction tank so as to penetrate the reaction tank, one side of the sparger tube being provided inside the reaction tank and being formed helically on the outer surface of the agitator as if surrounding the agitator, such that at least one kind of gas is transferred from the outside and supplied into the reaction tank by the sparger tube; and a gas mixing device provided inside the sparger tube such that, when the at least one kind of gas is transferred through the sparger tube, the gas is mixed.

The above prior art document states that the sparger tube has an end fabricated so as to twist in a helical shape; a hole is bored along a helical line such that mixed gas is discharged; the sparger tube is fabricated such that the helical line thereof surrounds the agitator; with reference to the agitator, gas discharged from the lower portion, center portion, and upper portion thereof can be evenly dispersed inside the reaction tank together with rotation of the agitator; and this advantageously optimizes the cell/microorganism cultivation environment and delays cell death, thereby maximizing the culture efficiency.

However, the cell culture device disclosed in the above prior art document still has a room for betterment and needs to be improved constantly for the following reasons.

For example, the reaction tank according to the above prior art document has such a structure that the complete medium and the cover are firmly coupled to each other and completely sealed; this structure makes it difficult to collect a sample for checking the degree of progress during cell culture; and, even if the cover is separated with some difficulty, the culture solution may be contaminated by inflow of outer air in the process of collecting the culture solution, thereby incurring the need for a structural improvement in order to prevent such problems.

In addition, the fact that a motor needs to be mounted to operate the agitator of the cell culture device makes it difficult to make the device itself compact (having a volume of 100 ml or less). This poses a limit to utilizing the same for multiple lab-based small-amount culture tests. Even if the device is made compact, mounting the motor, the agitator, or the like is costly and may generate manufacturing-related difficulty. Structural improvement is accordingly necessary.

Moreover, there is no mention of any feature for enabling the reaction container to directly adjust the acidity or basicity (pH) of the culture solution for optimal bioculture, failing to ensure the perfect condition for bioculture.

Meanwhile, conventional commercialized reaction containers either have a culture capacity of hundreds or thousands of litters for mass production or have a very small culture capacity of about 10 ml or less for laboratory-based research, and thus cannot facilitate cell culture conforming to the research purpose, that is, long-term culture and multiple sampling operations.

SUMMARY OF THE INVENTION

An aspect of the present disclosure is to provide a bioreaction container wherein the same is configured to enable easy and convenient assembly/formation such that the reaction container itself can be easily made compact; the reaction container itself is provided with a feature that enables direct adjustment of the acidity or basicity and a feature for providing necessary gases such that bioculture can proceed in an optimal condition; and a sample can be easily collected from the specimen that is being cultured while preventing an inflow of external alien substances.

In accordance with an aspect of the present disclosure, there is provided a bioreaction container including: a culture chamber configured to contain a culture solution and a life form in an inner space, the culture chamber having an open upper end; a chamber cover portion coupled to the upper end of the culture chamber, the chamber cover portion having a protruding tube provided on one side thereof so as to communicate with the inner space; a filter cap coupled to the protruding tube in an attachable/detachable manner so as to open/close the protruding tube; a gas introduction portion configured to penetrate the chamber cover portion and to communicate with the inner space so as to supply a predetermined gas into the inner space; and an acidity/basicity adjustment portion installed on the chamber cover portion while containing an adjustment solution that adjusts pH of the culture solution such that the adjustment solution is discharged into the inner space by pneumatic pressure.

The acidity/basicity adjustment portion may include: a storage tank having a containing space in which the adjustment solution is stored, the storage tank being mounted on the chamber cover portion so as to surround a surface of the protruding tube; a suction tube configured to penetrate/be coupled to the storage tank such that one end thereof is immersed in the adjustment solution; an air flow tube having one end configured to penetrate/be coupled to the chamber cover portion such that air supplied from the other end thereof flows into the inner space; and a discharge tube provided such that the other end of the suction tube and one side of the air flow tube communicate with each other.

The storage tank may include a first storage tank in which the adjustment solution that is acidic is stored and a second storage tank in which the adjustment solution that is basic is stored; and the suction tube, the air flow tube, and the discharge tube are formed so as to correspond to each of the first storage tank and the second storage tank.

The acidity/basicity adjustment portion may include: a storage tank having a containing space in which the adjustment solution is stored, the storage tank being mounted on the chamber cover portion so as to surround a surface of the protruding tube; an air introduction tube having one end configured to receive air and having the other end configured to penetrate/be coupled to the storage tank; an immersed tube having one end configured to communicate with the other end of the air introduction tube, the immersed tube being immersed in the adjustment solution in a bending shape, a microhole being formed in the immersed tube such that the adjustment solution flows therein; and an outflow tube having one end configured to communicate with the other end of the immersed tube and having the other end configured to penetrate/be coupled to the chamber cover portion.

The storage tank may include a first storage tank in which the adjustment solution that is acidic is stored and a second storage tank in which the adjustment solution that is basic is stored; and the air introduction tube, the immersed tube, and the outflow tube are formed so as to correspond to each of the first storage tank and the second storage tank.

The filter cap may include: a cap body configured as a tube body having a cavity formed therein and coupled to the protruding tube in an attachable/detachable manner; and a filtering filter coupled to one side of an inner peripheral surface of the cavity to be able to rotate downward while being supported elastically such that external alien substances moving into the cavity are filtered out, and air is allowed to move in/out.

The gas introduction portion may include: a first gas introduction tube configured to supply oxygen into the inner space; and a second gas introduction tube configured to supply carbon dioxide or nitrogen into the inner space.

The chamber cover portion may further include a protruding side wall formed to protrude upward along an outer peripheral surface thereof such that a mounting space is provided between the outer peripheral surface and the protruding tube, in which the gas introduction portion and the acidity/basicity adjustment portion are stably installed; and a corrugated portion is formed on the protruding side wall so as to prevent slipping.

At least one selected from a DO measurement sensor configured to measure the amount of dissolved oxygen in the culture solution, a pH measurement sensor configured to measure acidity/basicity of the culture solution, and a temperature sensor configured to measure the temperature of the culture solution, may be provided on one side of the culture chamber.

A barrier-type baffle having a through-hole formed therein may be mounted in the inner space of the culture chamber so as to facilitate mixing between the culture solution and the life form, or a protruding-type baffle may be formed so as to protrude from an inner surface of the culture chamber toward the inner space along a longitudinal direction of the culture chamber.

According to the present disclosure, a chamber cover portion coupled to a culture chamber, a filter cap coupled to a protruding tube of the chamber cover portion, and a gas introduction portion and an acidity/basicity adjustment portion, which are arranged on and coupled to the chamber cover portion, respectively, are assembled easily and conveniently such that a bioreaction container having necessary functions can be formed variously. This is advantageous in that not only the reaction container itself can be made compact easily, but can also be variously used for different laboratory-based small-amount culture tests.

In addition, one or two acidity/basicity adjustment portions capable of adjusting the acidity or basicity of the culture solution are selectively assembled/installed on the chamber cover portion such that each reaction container can be easily customized to the culture condition. This enables different kinds of culture tests to proceed rapidly under optimal conditions, thereby providing the experimenter with convenience.

Moreover, a filter cap is coupled to the protruding tube that communicates with the inner space of the culture chamber so as to prevent inflow of external alien substances, to maintain a uniform air pressure between the inner space and outer air, and to enable easy collection of the specimen that is being cultured without affecting the culture condition.

BRIEF DESCRIPTION OF THE DRAWINGS

The above and other aspects, features and advantages of the present disclosure will be more apparent from the following detailed description taken in conjunction with the accompanying drawings, in which:

FIG. 4 is mounted.

BRIEF DESCRIPTION OF REFERENCE SIGNS OF MAJOR PARTS IN THE DRAWINGS

Figure 1:
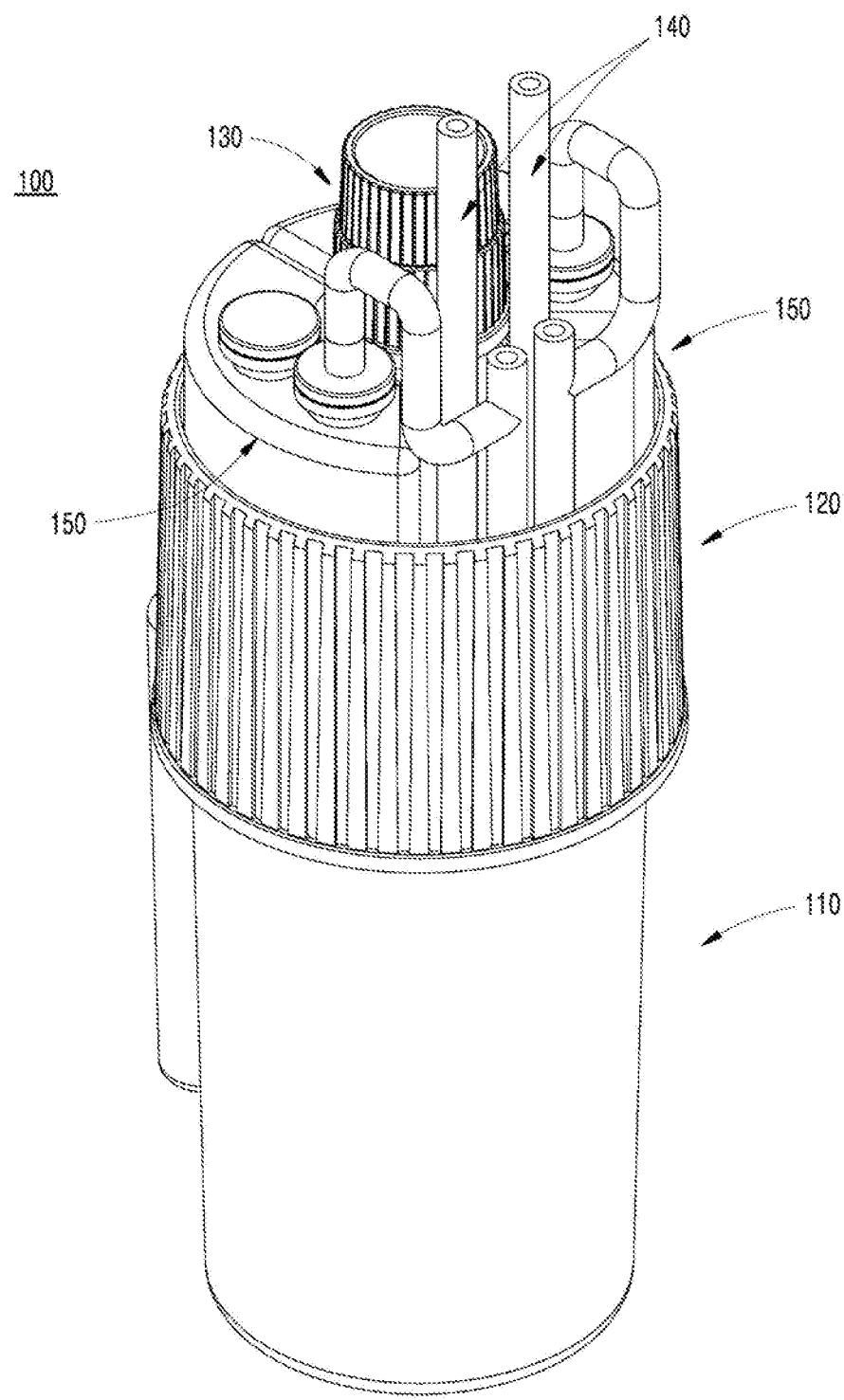
FIG. 1 is a perspective view of a bioreaction container according to an embodiment of the present disclosure.

S: adjustment solution
1: bioculture device
10: reaction container holder
20: shaking plate
30: display means
40: controller
100, 100': bioreaction container
110: culture chamber
111: inner space
112: baffle
112a: through-hole
120: chamber cover portion
121: mounting space
122: protruding tube
124: protruding side wall
124a: corrugated portion
130: filter cap
131: cavity
132: cap body
134: filtering filter
134a: elastic member
134b: filtering body
140: gas introduction portion
140a, 140b: first and second gas introduction tubes
150: acidity/basicity adjustment portion
151: containing space
152: storage tank
152a, 152b: first and second storage tanks
153: suction tube
154: air flow tube
155: discharge tube
156: air introduction tube
157: immersed tube
157a: microhole
158: outflow tube
160a, 160b, 160c: DO measurement sensor, pH measurement sensor, temperature sensor

DETAILED DESCRIPTION OF THE EXEMPLARY EMBODIMENTS

Hereinafter, exemplary embodiments of the present disclosure will be described in detail with reference to the accompanying drawings. In the description of the present disclosure, the description of the well-known function or structure will be omitted in order to clear the subject matter of the present disclosure.

Figure 2:
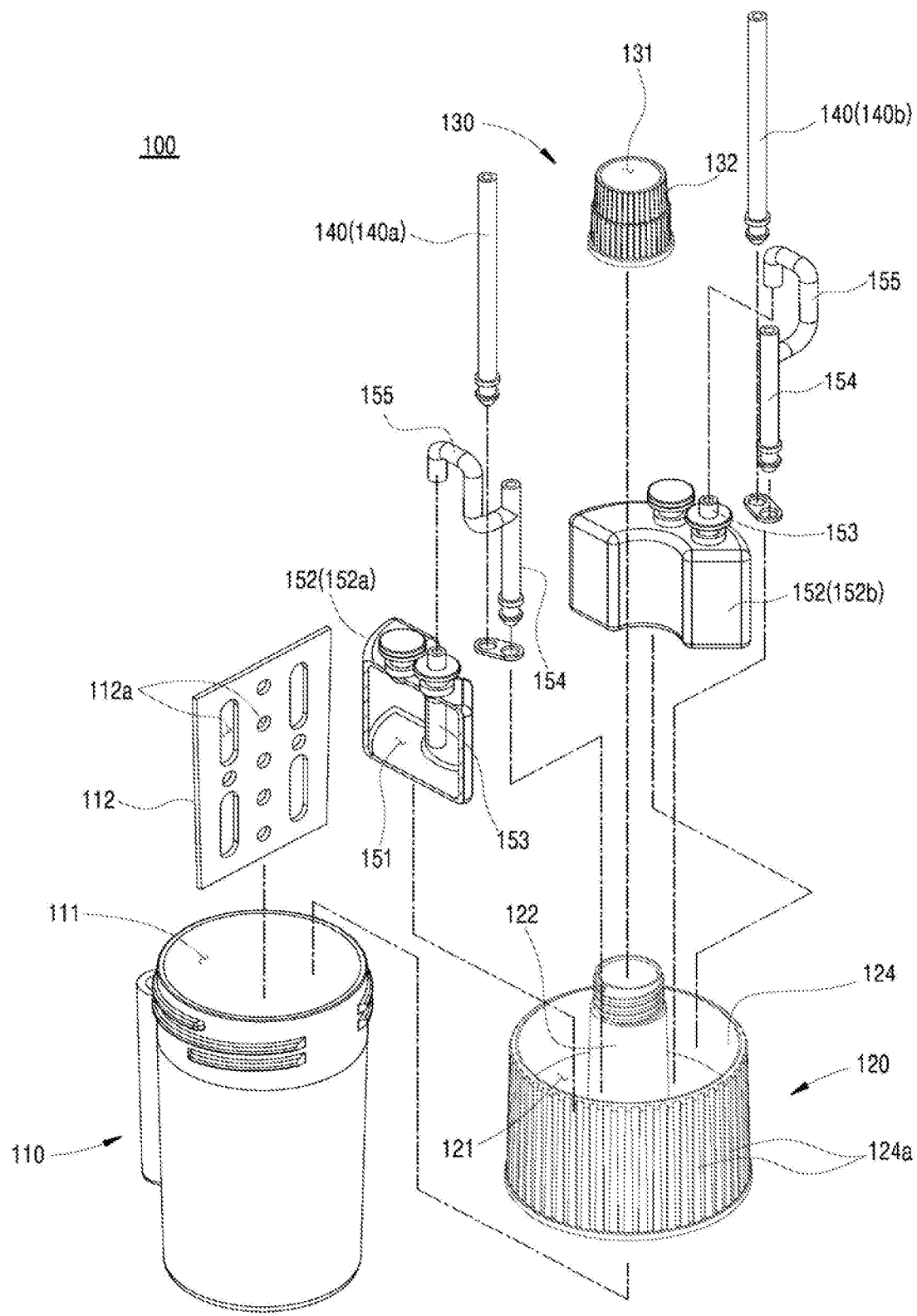
FIG. 2 is an exploded perspective view of FIG. 1.
Figure 3:
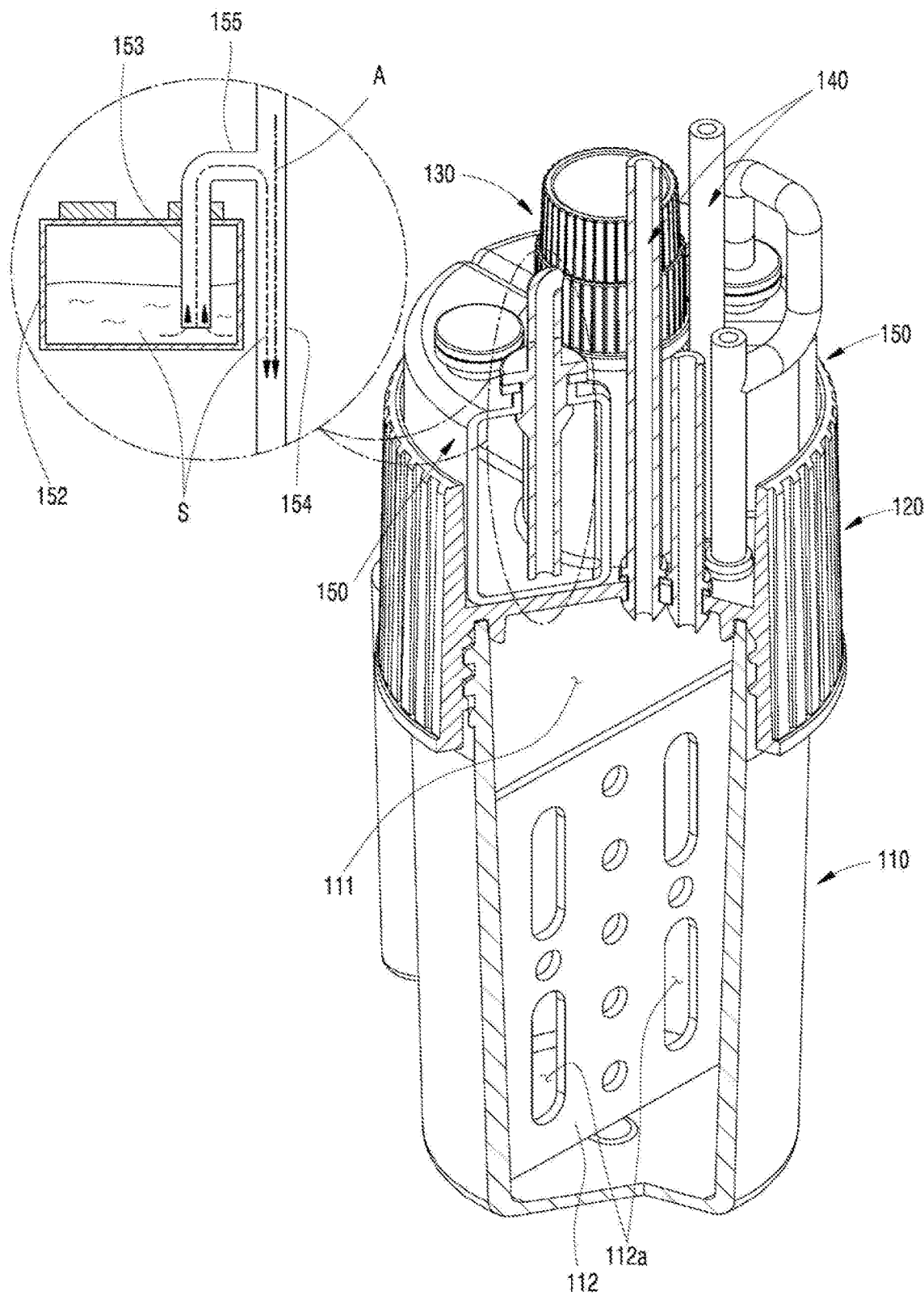
FIG. 3 is an operating state diagram illustrating the operating state of the acidity/basicity adjustment portion illustrated in FIG. 1.
Figure 4:
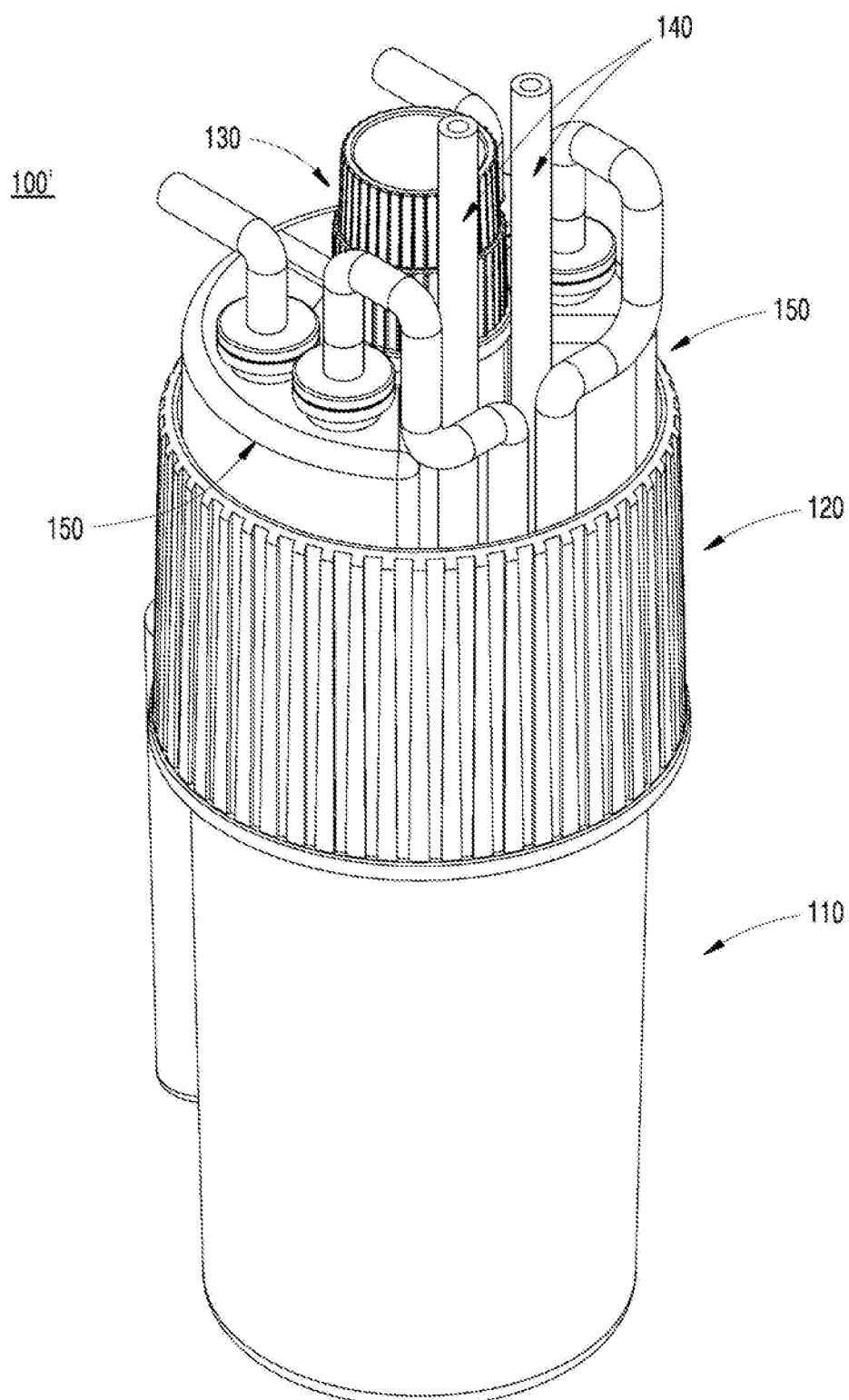
FIG. 4 is a perspective view of a bioreaction container according to a variant embodiment of the present disclosure.
Figure 5:
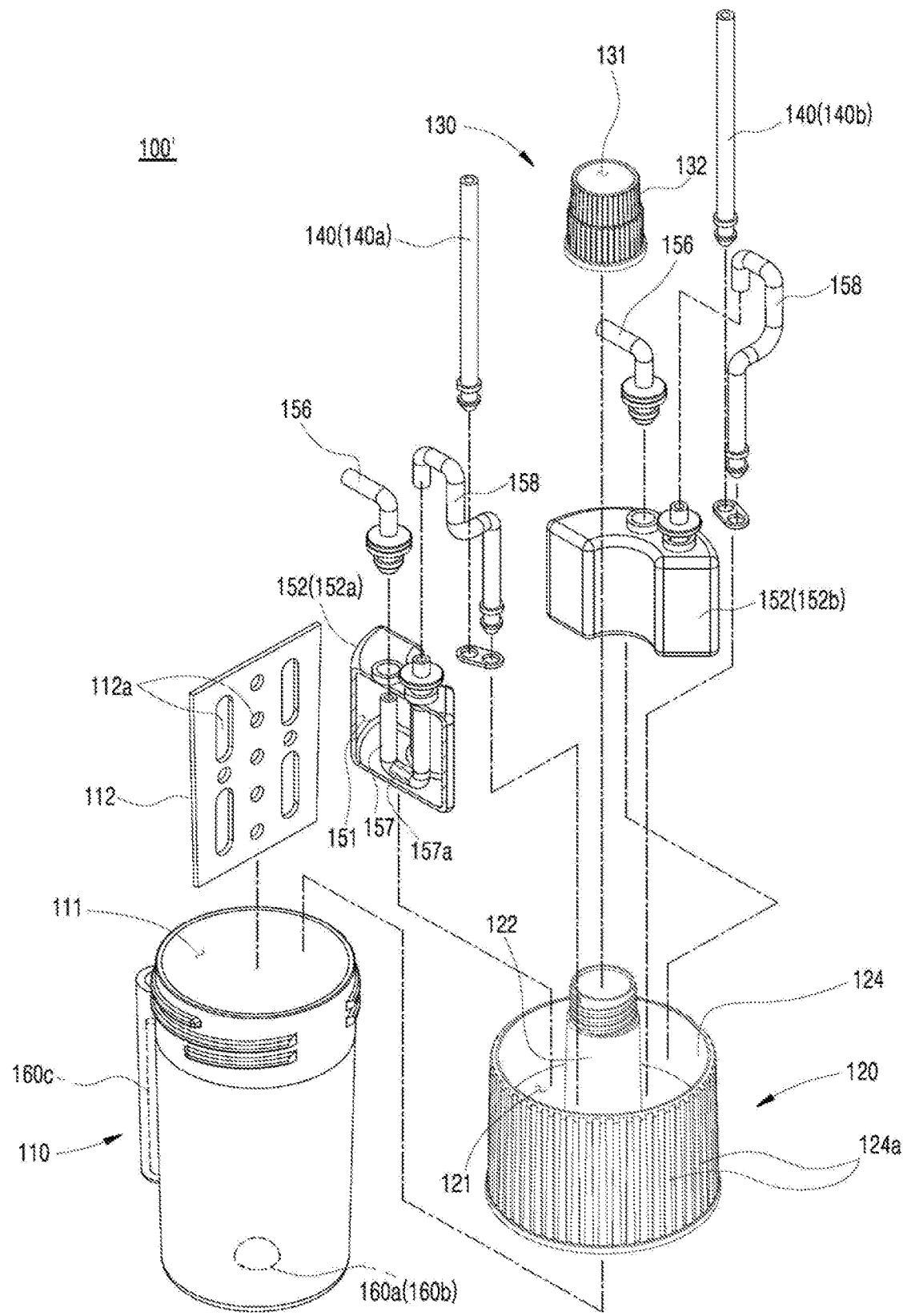
FIG. 5 is an exploded perspective view of FIG. 4.
Figure 6:
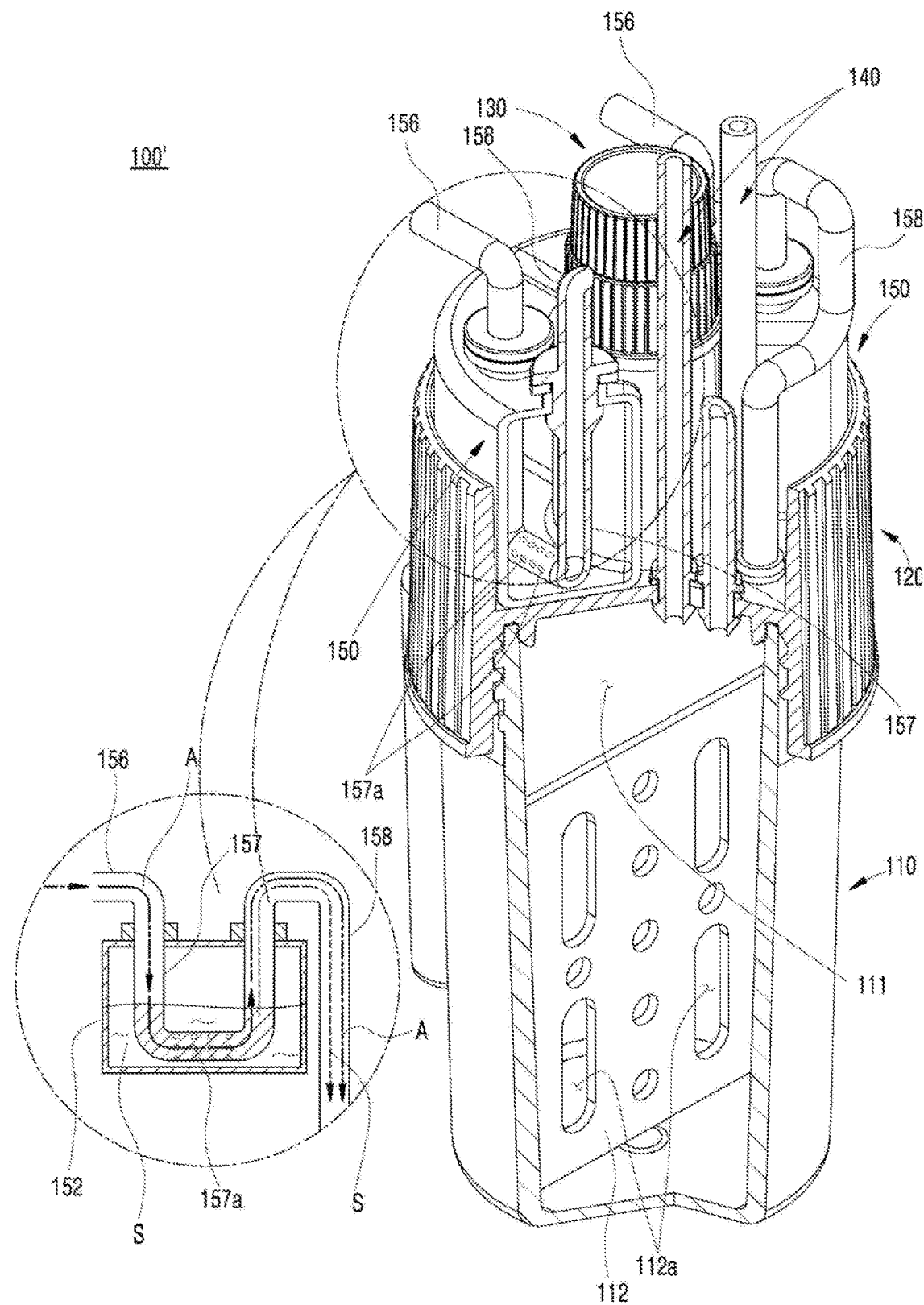
FIG. 6 is an operating state diagram illustrating the operating state of the acidity/basicity adjustment portion illustrated in FIG. 4.
Figure 7:
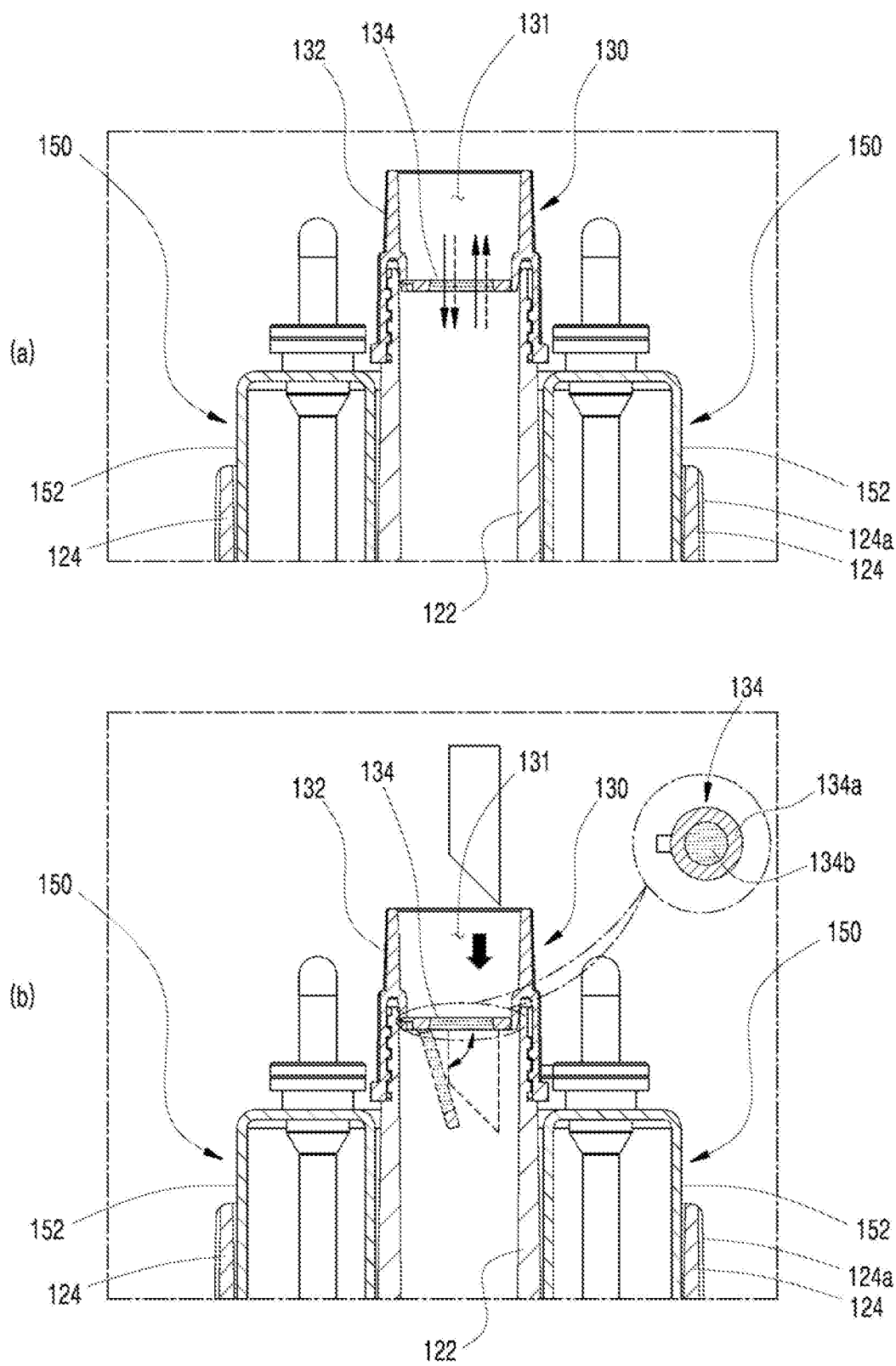
FIG. 7 is a sectional view illustrating the structure and operating state of the filter cap illustrated in FIG. 1 or FIG. 4.

FIG. 1 is a perspective view of a bioreaction container according to an embodiment of the present disclosure; FIG. 2 is an exploded perspective view of FIG. 1; FIG. 3 is an operating state diagram illustrating the operating state of the acidity/basicity adjustment portion illustrated in FIG. 1; FIG. 4 is a perspective view of a bioreaction container according to a variant embodiment of the present disclosure; FIG. 5 is an exploded perspective view of FIG. 4; FIG. 6 is an operating state diagram illustrating the operating state of the acidity/basicity adjustment portion illustrated in FIG. 4; FIG. 7 is a sectional view illustrating the structure and operating state of the filter cap illustrated in FIG. 1 or FIG. 4; and FIG. 8 is a diagram illustrating the overall structure of a bioculture device having a shaking function, a temperature-maintaining function, or the like, on which the bioreaction container in FIG. 1 or FIG. 4 is mounted.

In the detailed description of the disclosure and the claims, expressions that describe directions, such as upward (upper), downward (lower), leftward/rightward (side or lateral), forward (front), and rearward (back), are defined with reference to the relative position between elements or the drawings for the purpose of convenience of description, not for limiting the scope of the disclosure. Accordingly, respective directions described below are based thereof unless otherwise specified.

Figure 8:
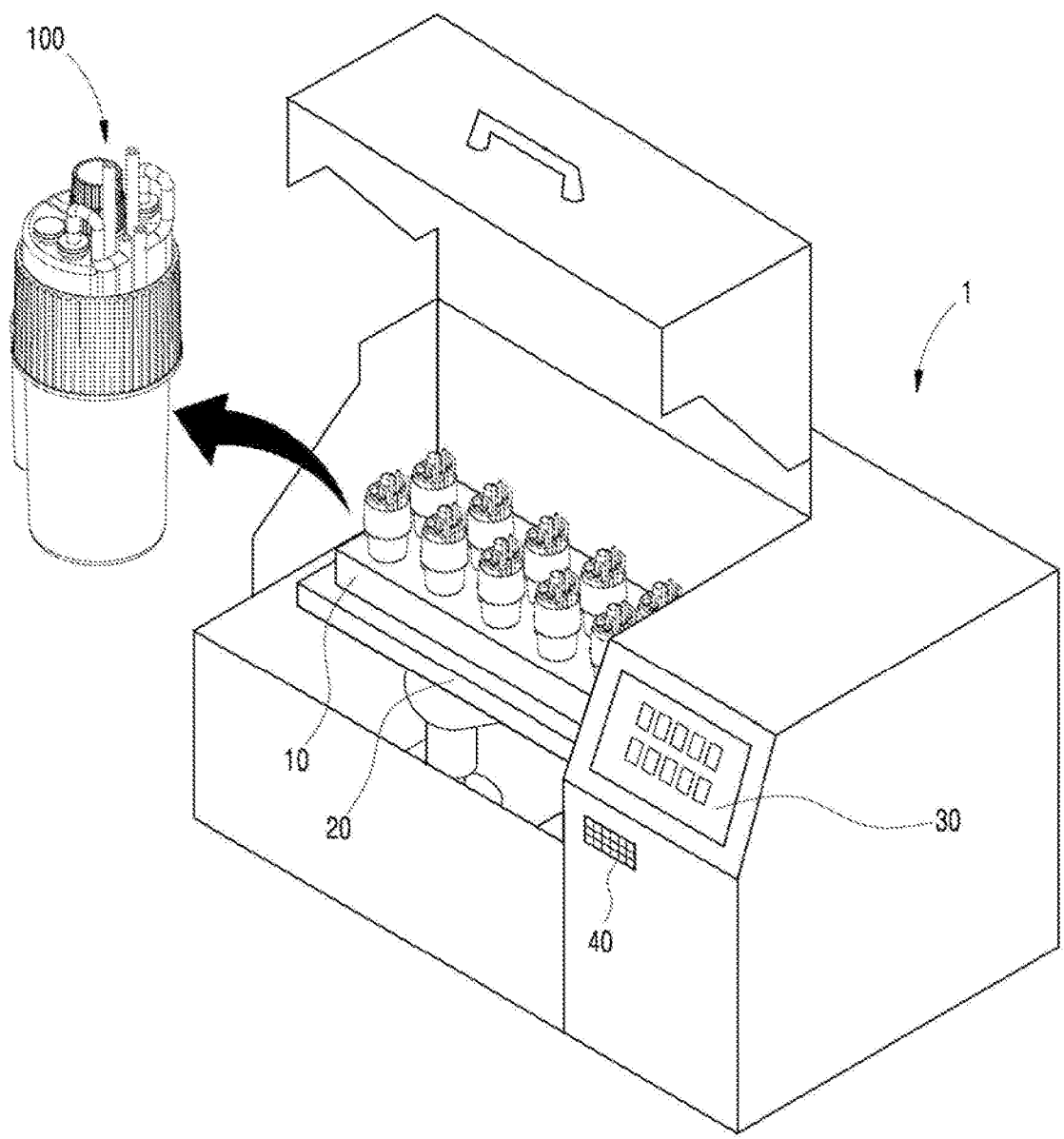
FIG. 8 is a diagram illustrating the overall structure of a bioculture device having a shaking function, a temperature-maintaining function, or the like, on which the bioreaction container illustrated in FIG. 1

A bioreaction container 100 to be described herein is, as illustrated in FIG. 8, a container used for a bioculture device 1 including: a reaction container holder 10 on which multiple reaction containers 100 are mounted; a shaking plate 20 configured to shake the reaction container holder 10; a display means 30 configured to display information measured by various sensors with regard to each reaction container 100; a controller 40 configured to control and set the operation of connected elements; an air line (not illustrated) configured to provide pneumatic pressure to each reaction container 100; and a gas supply line (not illustrated) configured to supply a specific gas necessary for culture.

The bioreaction container 100 according to the present disclosure has been envisioned to make the reaction container 100 itself compact through a structure that enables easy and convenient assembly/formation, to enable the reaction container 100 to directly adjust the acidity or basicity (pH) of the culture solution, and to easily collect a sample of the specimen that is being cultured, whenever necessary, while preventing inflow of alien substances from the outside. By envisioning such a bioreaction container 100, multiple laboratory-based small-amount culture tests can be performed quickly and conveniently under more active and optimized conditions.

In order to implement the above-described functions or operations, the bioreaction container 100 according to the present disclosure may include a culture chamber 110, a chamber cover portion 120, a filter cap 130, a gas introduction portion 140, and an acidity/basicity adjustment portion 150. Each element may be fabricated in an injection molding type using a synthetic resin material or in a diecasting type using a metallic material. This makes it possible to fabricate a precision-type compact bioreaction container 100 (having a volume of about 10 ml to 250 ml). Such a volume of the bioreaction container 100 facilitates laboratory-based long-term culture and multiple sampling operations, and there is a problem in that, in the case of a volume smaller than the same, sampling is difficult and, in the case of a volume larger than the same, administration and management are difficult, and the scale of the bioreaction device 1 increases excessively.

Hereinafter, each of the above-mentioned elements will be described in detail.

The culture chamber 110 is an element provided to contain a culture solution and a life form in the inner space 111 thereof, and may be configured in the shape of a vessel, the upper end of which is open, such that a liquid is contained therein. The culture chamber 110 may be configured in any shape as long as the same can contain liquid-state culture solution and a life form.

As illustrated in FIG. 1 and FIG. 2, the culture chamber 110 according to an embodiment of the present disclosure may have the shape of a cup, the width of which decreases downward, such that the same can be smoothly fitted and fixed to a reaction container holder 10, and may be fabricated through injection molding by using a material such as polystyrene (PS) resin which is superior in terms of moldability, shape stability, electric insulating characteristics, and resistance to chemicals, or polyvinyl chloride (PVC) resin, polycarbonate (PC) resin, or polypropylene (PP) resin which is superior in terms of anti-chemical characteristics, electric insulating characteristics, heat insulating characteristics, and resistance to corrosion. The culture chamber 110 is preferably made of a transparent material such that the state of the culture solution can be checked by the naked eye from the outside.

The culture chamber 110 may have a baffle 112 mounted in the inner space 111 thereof in a barrier type with a through-hole 112a formed therein as illustrated in FIG. 2. The baffle 112 serves as a resisting body against the culture solution that flows when rotated by the shaking plate 20 as illustrated in FIG. 8, thereby generating a turbulent or eddy current, such that the culture solution and the life form can be mixed efficiently.

Besides the above-described type of baffle 112, a protruding-type baffle (not illustrated) may be formed so as to protrude from the inner surface of the culture chamber 110 toward the inner space 111 such that the same is elongated along the longitudinal direction of the culture chamber 110. Multiple protruding-type baffles (not illustrated) may be formed to be spaced apart by a predetermined interval along the periphery of the inner peripheral surface of the culture chamber 110.

The chamber cover portion 120 is a cover-shaped element coupled to the upper end of the culture chamber 110 so as to prevent the culture solution and life form contained in the culture chamber 110 from moving out of the same. Besides this basic function, the chamber cover portion 120 provides a space in which a gas introduction portion 140 and an acidity/basicity adjustment portion 150 (described later) are mounted, and may have a protruding tube 122 formed to protrude upward from one side thereof so as to communicate with the inner space 111.

Any type of coupling between the chamber cover portion 120 and the culture chamber 110 is possible as long as the same can prevent the liquid material from moving outward. According to an embodiment of the present disclosure, the chamber cover portion 120 may be fastened to the culture chamber 110 through screw coupling so as to facilitate coupling with and decoupling from the culture chamber 110 as illustrated in FIG. 2, and rubber packing may be interposed between screw-coupling parts thereof so as to increase the degree of sealing between the same.

The chamber cover portion 120 may be fabricated through injection molding by using a material such as polystyrene (PS) resin, polyvinyl chloride (PVC) resin, polycarbonate (PC) resin, polypropylene (PP) resin, or polyethylene (PE) resin.

The protruding tube 122, which is formed so as to protrude upward from one side of the chamber cover portion 120 and to communication with the inner space 111, is an element provided such that a tool for collecting a sample from the specimen that is being cultured (for example, a pipette or a dropping pipette) is inserted while being guided easily and safely from the chamber cover portion 120 into the inner space 111, or removed therefrom.

The chamber cover portion 120 may have a protruding side wall 124 additionally formed to protrude upward along the outer peripheral surface thereof such that a mounting space 121 is formed between the outer peripheral surface thereof and the protruding tube 122, in which the gas introduction portion 140 and the acidity/basicity adjustment portion 150 are stably seated and installed. Such formation of the protruding side wall 124 guarantees that the gas introduction portion 140 and the acidity/basicity adjustment portion 150, installed therein, are stably supported without moving out of the chamber cover portion 120 in spite of shaking operations of the bioculture device 1.

The protruding side wall 124 may have corrugated portions 124a formed thereon so as to prevent slipping, and the corrugated portions 124a may be fabricated as protrusions formed to be elongated in the vertical direction while being spaced apart from each other as illustrated in FIG. 1, for example. The corrugated portions 124a ensure easy fastening and unfastening between the chamber cover portion 120 and the reaction container 100 in a screw coupling type without slipping out of the grasp of the experimenter.

The filter cap 130 is an element configured to selectively open or close the protruding tube 122 such that, when the same is opened, a sample collecting tool (for example, a pipette or a dropping pipette) is allowed to be inserted and, when the same is closed, alien substances are prevented from entering the inner space 111 from outside. The filter cap 130 may be fabricated in the shape of a cap that is coupled to the protruding tube 122 in an attachable/detachable manner.

Accordingly, the filter cap 130 may have any shape (including a bottle cap) as long as the protruding tube 122 can be selectively attached/detached and opened/closed. However, according to an embodiment of the present disclosure, the filter cap 130 may include a cap body 132 and a filtering filter 134 as illustrated in FIG. 7, and this structure corresponds to a technical feature unique to the present disclosure, not observable in the prior art.

The cap body 132 is a tube body having a cavity 131 formed therein and is configured to be coupled to the protruding tube 122 in an attachable/detachable manner. The cap body 132 is preferably screw-coupled to the protruding tube 122 so as to facilitate coupling and decoupling, and rubber packing may be interposed between the screw-coupling parts so as to increase the degree of sealing between the same.

The filtering filter 134 is a sheet-shaped element configured to filter out alien substances entering the cavity 131 while allowing air to move in/out. If a sample collecting tool (for example, a pipette or a dropping pipette) is inserted, the filtering filter 134 is thereby elastically deformed downward and rotated and, if the sample collecting tool is removed, the filtering filter 134 is elastically restored upward. The filtering filter 134 may be coupled to one side of the inner peripheral surface of the cavity 131 to be able to rotate downward while being arranged in a barrier type so as to delimit the cavity 131.

The filtering filter 134 may include a ring-shaped elastic member 134a, one end of which is coupled to the cavity 131 in an attachable/detachable manner, and a filtering body 134*b* provided at the center portion of the elastic member 134*a* so as to allow air or gas to pass and to prevent alien substances from passing. The filtering body 134*b* may be a nonwoven fabric, for example, and the degree of filtering may be selectively changed depending on the cultured life form.

The filter cap 130 according to an embodiment described above enables the experimenter to easily collect a sample of the specimen that is being cultured by using a pipette, a dropping pipette, or the like without having to decouple the filter cap 130 itself from the protruding tube 122, while efficiently preventing external alien substances from moving in. The filtering filter 134 may also be installed in the cavity 131 in a firmly fixed type without elastically deforming.

The gas introduction portion 140 is an element provided to supply a predetermined gas necessary to culture a life form into the inner space 111, and may be configured in the shape of a tube body which penetrates the chamber cover portion 120, communicates with the inner space 111, and which is connected to the gas supply line (not illustrated) of the bioculture device 1 described above. A packing member may be provided in the area in which the gas introduction portion 140 penetrates the chamber cover portion 120, and the inner diameter of the tube body may be formed to have various sizes as needed.

The gas introduction portion 140 may have the shape of a tube body made of a metallic material, synthetic resin, or silicone such that outer atmosphere and the inner space 111 communicate with each other. If necessary, the gas introduction portion 140 may be fabricated in a bending shape, and multiple gas introduction portions 140 may be installed depending on the cultured life form.

The gas introduction portion 140 according to an embodiment of the present disclosure includes a first gas introduction tube 140*a* and a second gas introduction tube 140*b* as illustrated in FIG. 1 and FIG. 2. The first gas introduction tube 140*a* is an element provided to supply the inner space 111 with oxygen that is necessary to culture a life form, and the second gas introduction tube 140*b* is an element provided to supply the inner space 111 with carbon dioxide or nitrogen, which is secondarily necessary to culture a life form.

The first and second gas introduction tubes 140*a* and 140*b* are provided separately such that oxygen or the like is not mixed during supply with other gases such as carbon dioxide and nitrogen, thereby making it possible to selectively provide the culture solution with necessary gases under optimal conditions according to conditions to culture a life form, and the amount of introduced gases may be controlled by the controller 40 of the bioculture device 1 described above.

The acidity/basicity adjustment portion 150 is an element provided to ensure that each life form is cultured at the required optimal acidity or basicity, and to supply an adjustment solution S that is customized according to the characteristics of each cultured life form such that a differentiated test can be performed stably. The acidity/basicity adjustment portion 150 may be configured in a tank shape so as to contain an adjustment solution S for adjusting the pH of the culture solution, and may be installed on the chamber cover portion 120. The contained adjustment solution S may be either an acidic solution or a basic solution, and may include various minerals necessary to grow the life form.

The acidity/basicity adjustment portion 150 is a technical feature of the present disclosure distinguished from the prior art, and may be configured in any structure and type as long as the adjustment solution S contained in the inner space 111 of the culture chamber 110 is discharged by pneumatic pressure provided by the air line (not illustrated) of the bioculture device 1.

The acidity/basicity adjustment portion 150 according to an embodiment of the present disclosure may include a storage tank 152, a suction tube 153, an air flow tube 154, and a discharge tube 155 as illustrated in FIG. 2 and FIG. 3.

The storage tank 152 is an element which has a containing space 151 provided therein such that an adjustment solution S is stored therein, and which is mounted on the chamber cover portion 120 so as to surround a surface of the protruding tube 122. Specifically, the storage tank 152 is configured as an arc-shaped barrel fitted/fixed to a mounting space 121 defined by the chamber cover portion 120, the protruding tube 122, and the protruding side wall 124, and is fixed to the chamber cover portion 120 firmly and stably.

The storage tank 152 may be fabricated through injection molding by using a material such as polystyrene (PS) resin, polyvinyl chloride (PVC) resin, polycarbonate (PC) resin, polypropylene (PP) resin, or polyethylene (PE) resin. The size of the arc shape of the storage tank 152 may be varied as long as there is no mounting interference with the gas introduction portion 140 that penetrates the chamber cover portion 120 or with tube bodies (described later).

The storage tank 152 may be configured not only in a single barrel structure, but also in a split structure so as to include a first storage tank 152*a* in which an acidic adjustment solution S is stored and a second storage tank 152*b* in which a basic adjustment solution S is stored, as in an embodiment of the present disclosure and a variant embodiment thereof illustrated in FIG. 1 to FIG. 5.

Such a structure as including two separate tanks enables selective adjustment of acidity and basicity simultaneously or with a time difference such that culture experiments can proceed continuously in various types and conditions, and provides a convenience in that, if the acidity or basicity is adjusted erroneously, a predetermined amount of adjustment solution (S) having the opposite property can be introduced instantly so as to neutralize the culture solution.

The suction tube 153 is an element which penetrates/is coupled to the storage tank 152 such that one end thereof is immersed in the adjustment solution S. The air flow tube 154 is an element, one end of which penetrates/is coupled to the chamber cover portion 120 such that air supplied from the other end thereof moves to the inner space 111. The discharge tube 155 is an element provided such that the other end of the suction tube 153 and one side of the air flow tube 154 communicate with each other.

The adjustment solution S is discharged through the above-described tube body structure on the basis of Bernoulli's principle, which will be described briefly with reference to FIG. 3. Bernoulli's principle is described in terms of an equation that describes the relationship between the velocity, pressure, and potential energy of a fluid, and states that the sum of all forms of energy in a fluid along a streamline is the same at all points on that streamline. This principle is a widely known natural law, and detailed description thereof will be omitted herein.

Referring to the magnified operating state diagram of FIG. 3, if air rapidly flows (A) toward the inner space 111 through the air flow tube 154 connected to the air line (not illustrated) of the bioculture device 1, a negative pressure is generated in the discharge tube 155. Accordingly, the adjustment solution S is suctioned into the discharge tube 155 through the suction tube 153, and the adjustment solution S suctioned into the discharge tube 155 is introduced into the inner space 111 through the air flow tube 154.

That is, the inside of the air flow tube 154 reaches a low-pressure state as a result of the fast flow A of air, and the inside of the discharge tube 155, one side of which communicates with the air flow tube 154, reaches a high-pressure state. As a result, the adjustment solution S is naturally suctioned and discharged into the inner space 111 along the suction tube 153, the discharge tube 155, and the air flow tube 154 (refer to Bernoulli's principle).

The tube bodies according to an embodiment described above are made of a metallic material, synthetic resin, or silicone, and may be fabricated in variously bending shapes according to the connection structure. The suction tube 153 and the discharge tube 155, to which suction force is applied, are preferably formed to have a tube-body inner diameter smaller than that of the air flow tube 154 such that suction occurs not only by the negative pressure, but also by the osmotic pressure. For example, the suction tube 153 and the discharge tube 155 are preferably fabricated as tube bodies having a diameter of about 1 mm to 3 mm.

When the storage tank 152 is configured in a split structure and includes a first storage tank 152a and a second storage tank 152b as described above, the suction tube 153, the air flow tube 154, and the discharge tube 155 may be arranged and connected so as to correspond to each of the first storage tank 152a and the second storage tank 152b in the same manner as described above.

The acidity/basicity adjustment portion 150 according to a variant embodiment of the present disclosure may include a storage tank 152, an air introduction tube 156, an immersed tube 157, and an outflow tube 158 as illustrated in FIG. 4 to FIG. 6 in detail.

The storage tank 152 has the same structure as in the case of the above-described embodiment, except for a minor difference in connection with the portion penetrated by/coupled to a tube body, so repeated description thereof will be omitted herein. The storage tank 152 according to the variant embodiment may be configured not only in a single barrel structure, but also in a split structure so as to include a first storage tank 152a in which an acidic adjustment solution S is stored and a second storage tank 152b in which a basic adjustment solution S is stored, as in the embodiment of the present disclosure and the variant embodiment illustrated in FIG. 1 to FIG. 5.

Such a structure which includes two separate tanks enables selective adjustment of acidity and basicity simultaneously or with a time difference such that culture experiments can proceed continuously in various types and conditions, and provides convenience in that, if the acidity or basicity is adjusted erroneously, a predetermined amount of adjustment solution (S) having the opposite property can be introduced instantly so as to neutralize the culture solution.

The air introduction tube 156 is an element, one end of which communicates with the air line of the bioculture device 1 so as to receive air, and the other end of which penetrates/is coupled to the storage tank 152. The immersed tube 157 is an element, one end of which communicates with the other end of the air introduction tube 156, which is immersed in the adjustment solution S in a bending type, and which has a microhole 157a formed therein such that the adjustment solution S flows in through the immersed area. The outflow tube 158 is an element, one end of which communicates with the other end of the immersed tube 157, and the other end of which penetrates/is coupled to the chamber cover portion 120 so as to communicate with the inner space 111.

The principle according to which the adjustment solution S is discharged through the tube body structure according to the variant embodiment described above will be described with reference to the magnified operating state diagram of FIG. 6. Air supplied from the air line (not illustrated) of the bioculture device 1 flows (A) to the immersed tube 157 through the air introduction tube 156. The adjustment solution S, which has flowed into the immersed tube 157 through the microhole 157a formed in the immersed tube 157, is continuously moved (A) toward the outflow tube 158 by the supplied air, and is then introduced into the inner space 111 of the culture chamber 110. While the adjustment solution S is introduced through the outflow tube 158 in this manner, the adjustment solution S is continuously supplemented into the immersed tube 157 through the microhole 157a.

The tube bodies according to the variant embodiment described above are likewise made of a metallic material, synthetic resin, or silicone, and may be fabricated in variously bending shapes according to the connection structure. The variant embodiment adopts such a scheme that the adjustment solution S that has flowed into the immersed tube 157 is pushed to the inner space 111 through the outflow tube 158 by air pressure, and the tube-body inner diameter of the immersed tube 157 may be sufficiently smaller than that of the air introduction tube 156 or the outflow tube 158. However, the immersed tube 157 preferably has an inner diameter of about 1 mm to 3 mm such that the reaction container 100' can be made compact.

When the storage tank 152 is configured in a split structure and includes a first storage tank 152a and a second storage tank 152b as described above, the air introduction tube 156, the immersed tube 157, and the outflow tube 158 may be arranged and connected so as to correspond to each of the first storage tank 152a and the second storage tank 152b.

The bioreaction containers 100 and 100' according to the present disclosure, described above, may have various kinds of sensor devices such that multiple reaction containers 100 mounted on the bioculture device 1 illustrated in FIG. 8 can be both individually monitored and individually controlled.

Specifically, at least one selected from a DO measurement sensor 160a configured to measure the amount of dissolved oxygen in the culture solution, a pH measurement sensor 160b configured to measure the acidity/basicity of the culture solution, and a temperature sensor 160c configured to measure the temperature of the culture solution, may be provided on one side of the culture chamber 110 as illustrated in FIG. 5.

The DO measurement sensor 160a and the pH measurement sensor 160b may be patch-type sensors installed on one side of the lower end of the inner space 111 to be able to make a direct contact with the culture solution. The patch-type DO measurement sensor 160a and the pH measurement sensor 160b measure the DO inside the culture solution and the pH of the culture solution in real time by interworking with optical devices provided on the lower end of the reaction container holder 10 of the bioculture device 1 so as to emit light in the visible ray domain toward the corresponding sensors and to receive light reflected by the sensors.

Information measured by the patch-type DO measurement sensor 160a, the pH measurement sensor 160b, and the optical devices, which interwork therewith, in this manner is transmitted to the bioculture device 1. The controller 40 may perform an operation of controlling the gas introduction portion 140 or controlling the acidity/basicity adjustment portion 150 so as to maintain an appropriate culture condition. The corresponding information may be displayed through the display means 30 in real time.

The temperature sensor 160c is mounted on the outer surface of the culture chamber 110 so as to measure the temperature of the culture solution in real time. The bioculture device 1 may receive the measured culture solution temperature information while being electrically connected to the temperature sensor 160c and may display the corresponding information in real time through the display means 30.

Although not illustrated in the drawings, a thermoelectric element plate may be installed on one side of the culture chamber 110 or on the culture container holder 10 while being electrically connected to the bioculture device 1 such that the temperature of the contained culture solution can be increased/decreased. This makes it possible to control the temperature of the culture solution by the controller 40 of the bioculture device 1 such that the same is controlled and individually increased/decreased so as to maintain an optimal culture condition.

As described above, the gas introduction portion 140, the acidity/basicity adjustment portion 150, the DO measurement sensor 160a, the pH measurement sensor 160b, the temperature sensor 160c, and the thermoelectric element plate (not illustrated) are mounted as a single unit on the bioreaction container 100, which is connected to the bioculture device 1 and operates while interworking therewith, such that the state of the introduced culture solution can be monitored in real time, and free sampling can be conducted while maintaining optimal culture conditions (DO, pH, and temperature).

Although the specific embodiment of the present disclosure has been described above, it is apparent to those skilled in the art that the present disclosure is not limited to the embodiment disclosed herein and various modifications and changes can be made without departing from the spirit and scope of the present disclosure. Therefore, such modifications and changes should not be individually construed from the spirit or point of view of the present disclosure, and it should be understood that modified embodiments belong to the claims of the present disclosure.

INDUSTRIAL APPLICABILITY

According to a bioreaction container according to the present disclosure, elements constituting the same can be assembled easily and conveniently so as to variously form a bioreaction container having necessary functions. Accordingly, the reaction container itself can be made compact, and can be utilized in various manners for different laboratory-based small-amount culture tests. Such tests can be performed rapidly under optimal conditions, thereby providing the experimenter with convenience. As such, the bioreaction container according to the present disclosure has usability in connection with the prior art, and not only provides a sufficient possibility of marketing or commercial availability of devices to which the same is applied, beyond the limit of the prior art, but also can be implemented clearly on a practical basis. Therefore, the present disclosure has an industrial applicability.

What is claimed is:

1. A bioreaction container comprising:
a culture chamber configured to contain a culture solution and a life form in an inner space, the culture chamber having an open upper end;
a chamber cover portion coupled to the upper end of the culture chamber, the chamber cover portion having a protruding tube provided on one side thereof so as to communicate with the inner space;
a filter cap coupled to the protruding tube in an attachable/detachable manner so as to open/close the protruding tube;
a gas introduction portion configured to penetrate the chamber cover portion and to communicate with the inner space so as to supply a predetermined gas into the inner space; and
an acidity/basicity adjustment portion installed on the chamber cover portion while containing an adjustment solution that adjusts pH of the culture solution such that the adjustment solution is discharged into the inner space by pneumatic pressure, wherein
acidity/basicity adjustment portion comprises:
a storage tank having a containing space in which the adjustment solution is stored, the storage tank being mounted on the chamber cover portion so as to surround a surface of the protruding tube;
an air introduction tube configured to introduce air supplied from outside to the storage tank; and
an outflow tube configured such that the adjustment solution is introduced into the inner space by pneumatic pressure provided through the air introduction tube, wherein the chamber cover portion has a protruding side wall formed to protrude in a direction of the protruding tube upward along an outer peripheral surface thereof and has an annular mounting space provided between the protruding side wall and the protruding tube, and the storage tank is installed in the mounting space.

2. The bioreaction container of claim 1, wherein the storage tank comprises a first storage tank in which the adjustment solution that is acidic is stored and a second storage tank in which the adjustment solution that is basic is stored; and air introduction tube and the outflow tube are formed so as to correspond to each of the first storage tank and the second storage tank.

3. The bioreaction container of claim 1, wherein the storage tank is formed in an arc-shaped barrel structure so as to be fitted/fixed within the annular mounting space along a circumferential direction of the chamber cover portion such that there is no mounting interference with the gas introduction portion in the annular mounting space.

4. The bioreaction container of claim 1, wherein the storage tank comprises a first storage tank in which the adjustment solution that is acidic is stored and a second storage tank in which the adjustment solution that is basic is stored; and the storage tank is formed in an arc-shaped barrel structure so as to be fitted/fixed to the annular mounting space along a circumferential direction of the chamber cover portion such that there is no mounting interference with the gas introduction portion in the annular mounting space.

5. The bioreaction container of claim 1, wherein the acidity/basicity adjustment portion comprises:
a storage tank having a containing space in which the adjustment solution is stored, the storage tank being mounted on the chamber cover portion so as to surround a surface of the protruding tube;
a suction tube configured to penetrate/be coupled to the storage tank such that one end thereof is immersed in the adjustment solution;
an air flow tube having one end configured to penetrate/be coupled to the chamber cover portion such that air supplied from the other end thereof flows into the inner space; and a discharge tube provided such that the other end of the suction tube and one side of the air flow tube communicate with each other.

6. The bioreaction container of claim 1, wherein the acidity/basicity adjustment portion comprises:
a storage tank having a containing space in which the adjustment solution is stored, the storage tank being mounted on the chamber cover portion so as to surround a surface of the protruding tube;
an air introduction tube having one end configured to receive air and having the other end configured to penetrate/be coupled to the storage tank;
an immersed tube having one end configured to communicate with the other end of the air introduction tube, the immersed tube being immersed in the adjustment solution in a bending shape, a microhole being formed in the immersed tube such that the adjustment solution flows therein; and
an outflow tube having one end configured to communicate with the other end of the immersed tube and having the other end configured to penetrate/be coupled to the chamber cover portion.

7. The bioreaction container of claim 1, wherein the filter cap comprises:
a cap body configured as a tube body having a cavity formed therein and coupled to the protruding tube in an attachable/detachable manner; and
a filtering filter coupled to one side of an inner peripheral surface of the cavity to be able to rotate downward while being supported elastically such that external alien substances moving into the cavity are filtered out, and air is allowed to move in/out.

8. The bioreaction container of claim 1, wherein the gas introduction portion comprises:
a first gas introduction tube configured to supply oxygen into the inner space; and
a second gas introduction tube configured to supply carbon dioxide or nitrogen into the inner space.

9. The bioreaction container of claim 1, wherein at least one selected from a DO measurement sensor configured to measure the amount of dissolved oxygen in the culture solution, a pH measurement sensor configured to measure acidity/basicity of the culture solution, and a temperature sensor configured to measure the temperature of the culture solution, is provided on one side of the culture chamber.

10. The bioreaction container of claim 1, wherein a barrier-type baffle having a through-hole formed therein is mounted in the inner space of the culture chamber so as to facilitate mixing between the culture solution and the life form, or a protruding-type baffle is formed so as to protrude from an inner surface of the culture chamber toward the inner space along a longitudinal direction of the culture chamber.

11. The bioreaction container of claim 1, wherein the storage tank is mounted on the chamber cover portion such that a bottom of the containing space in which the adjustment solution is stored is above a top of the inner space of the culture chamber.

12. The bioreaction container of claim 1, further comprising an immersed tube having a first end connected to an end of the air introduction tube to receive the air introduced into the storage tank by the air introduction tube and a second end connected to an end of the outflow tube to deliver the adjustment solution by the pneumatic pressure to the outflow tube.

* * * * *